US008813569B2

(12) United States Patent
Abe et al.

(10) Patent No.: US 8,813,569 B2
(45) Date of Patent: Aug. 26, 2014

(54) ULTRASONIC SENSOR

(75) Inventors: Yutaka Abe, Watarai-gun (JP); Hiroyuki Toyoda, Tsu (JP)

(73) Assignee: Panasonic Corporation, Osaka (JP)

( * ) Notice: Subject to any disclaimer, the term of this patent is extended or adjusted under 35 U.S.C. 154(b) by 566 days.

(21) Appl. No.: 13/102,421

(22) Filed: May 6, 2011

(65) Prior Publication Data

US 2011/0277550 A1 Nov. 17, 2011

(30) Foreign Application Priority Data

May 14, 2010 (JP) .................................. 2010-112529

(51) Int. Cl.
*G01N 29/04* (2006.01)

(52) U.S. Cl.
USPC .......................................................... 73/632

(58) Field of Classification Search
USPC ............. 73/632, 643, 649, 702; 340/436, 435
See application file for complete search history.

(56) References Cited

U.S. PATENT DOCUMENTS

| | | | |
|---|---|---|---|
| 4,918,672 A | | 4/1990 | Iwabuchi et al. |
| 5,745,050 A | * | 4/1998 | Nakagawa .................... 340/903 |
| 6,089,106 A | * | 7/2000 | Patel et al. ................ 73/862.582 |
| 6,532,193 B1 | * | 3/2003 | Fehse et al. ................... 367/140 |
| 6,627,501 B2 | | 9/2003 | Su |
| 6,759,950 B2 | * | 7/2004 | Nishimoto et al. ........... 340/436 |
| 7,317,663 B2 | * | 1/2008 | Kawashima et al. ......... 367/188 |
| 7,392,705 B2 | * | 7/2008 | Kawashima et al. ........... 73/632 |
| 7,522,474 B2 | | 4/2009 | Nakajima et al. |
| 7,902,968 B2 | * | 3/2011 | Kojima et al. ................ 340/435 |
| 2007/0267941 A1 | | 11/2007 | Eidel et al. |
| 2012/0240680 A1 | * | 9/2012 | Urase et al. ..................... 73/632 |
| 2013/0214642 A1 | * | 8/2013 | Lin et al. ....................... 310/319 |

FOREIGN PATENT DOCUMENTS

| | | |
|---|---|---|
| DE | 10 2005 005 331 | 8/2006 |
| JP | 62-140378 | 9/1987 |
| JP | 62-163781 | 10/1987 |
| JP | 2007-256515 | 10/2007 |
| JP | 2010-025674 | 2/2010 |

OTHER PUBLICATIONS

The extended European search report dated Jan. 31, 2012.
Office Action dated Nov. 28, 2013 issued in corresponding Japanese application No. 2010-112529 and the English summary thereof.

* cited by examiner

*Primary Examiner* — J M Saint Surin
(74) *Attorney, Agent, or Firm* — Bacon & Thomas, PLLC

(57) ABSTRACT

An ultrasonic sensor includes an ultrasonic element. The ultrasonic element includes an ultrasonic oscillator for sending, receiving or transceiving ultrasonic waves, an element body having an opening for passage of ultrasonic waves formed on one surface, the ultrasonic oscillator being arranged within the element body, and terminal portions protruding from the element body to feed an electric current to the ultrasonic oscillator. The ultrasonic sensor further includes a housing having an opening formed on one surface for communication with the opening of the element body. The housing includes a receiving portion for receiving the ultrasonic element and a positioning portion integrally formed with the receiving portion to position the ultrasonic element in place. The ultrasonic sensor includes a printed wiring board arranged to interpose the ultrasonic element between the printed wiring board and the receiving portion. The terminal portions of the ultrasonic element are mounted to the printed wiring board.

4 Claims, 12 Drawing Sheets

ULTRASONIC SENSOR

FIELD OF THE INVENTION

The present invention relates to an ultrasonic sensor for use in sending, receiving or transceiving ultrasonic waves.

BACKGROUND OF THE INVENTION

Conventionally, there are known ultrasonic sensors or ultrasonic switches used for detection of objects or other purposes. They are disclosed in, e.g., Japanese Utility Model Laid-open Publication Nos. S62-163781 and S62-140378. The ultrasonic elements disclosed in these prior art documents are covered with elastic members for an anti-vibration purpose and are so-called closed ultrasonic elements that generate ultrasonic waves by the vibration of an element body itself. In addition to the closed ultrasonic elements, there are known so-called open ultrasonic elements in which an ultrasonic oscillator is arranged within an element body with an opening on one surface so that ultrasonic waves generated by the oscillator can be transmitted through the opening. A conventional ultrasonic sensor using the open ultrasonic elements will now be described with reference to FIGS. 7A and 7B. In the following description, the direction running toward the upper and lower sides in FIG. 7A is defined as an up-down direction.

Referring to FIGS. 7A and 7B, the conventional ultrasonic sensor makes use of an ultrasonic element 100 that includes a cylindrical element body 100a having a bottom with an opening (not shown) for transceiving ultrasonic waves and an ultrasonic oscillator (not shown) arranged within the element body 100a to transceive ultrasonic waves. The ultrasonic element 100 is stored in a cylindrical receiving portion 200a having a bottom, which is provided in a rectangular box-shaped body 200 with an open top. The body 200 is coupled with a rectangular box-shaped cover 201 having an open bottom with the openings thereof facing each other. The body 200 and the cover 201 make up a housing 202.

A flat printed wiring board 203 is fixed to the body 200 by set screws 205. The printed wiring board 203 includes at least one of a drive circuit for driving the ultrasonic element 100 in response to a drive signal from outside and a converter circuit for converting ultrasonic waves received by the ultrasonic element 100 to a wave-receiving signal.

The ultrasonic element 100 is provided with a pair of terminal portions 100b on the upper surface of the element body 100a and is stored in the receiving portion 200a with the terminal portions 100b facing toward the opening of the body 200. The terminal portions 100b are soldered to the printed wiring board 203. In the bottom of the receiving portion 200a, there is formed a communication hole 200b communicating with the opening of the ultrasonic element 100 and the outside. The communication hole 200b serves as a horn that expands the wave-transceiving range of ultrasonic waves and decides the directivity of ultrasonic waves.

Since the element body 100a does not vibrate in the open ultrasonic element 100 described above, there is no need to use an elastic member for an anti-vibration purpose. However, when storing the ultrasonic element 100 in the receiving portion 200a, it is difficult to correctly position the ultrasonic element 100 due to the gap between the ultrasonic element 100 and the receiving portion 200a. This may make the center of the communication hole 200b and the center of the opening of the ultrasonic element 100 misaligned, which affects the directivity of ultrasonic waves. Thus, variations occur in the directivity of ultrasonic waves, possibly worsening the detection performance. For the reasons noted above, a cylindrical elastic member 204 is attached to the ultrasonic element 100 in the conventional ultrasonic sensor as shown in FIG. 7A, thereby filling up the gap between the receiving portion 200a and the ultrasonic element 100. As a result, the ultrasonic element 100 is brought into contact with the elastic member 204 under pressure and, therefore, is correctly positioned within the storage unit 200a. This makes it possible to solve the problems mentioned above.

In the conventional ultrasonic sensor, however, the step of attaching the elastic member 204 to the ultrasonic element 100 prolongs the manufacturing time of the ultrasonic sensor because the elastic member 204 needs to be attached to the ultrasonic element 100. Moreover, the manufacturing efficiency is reduced because the step of attaching the elastic member 204 to the ultrasonic element 100 is time-consuming. In addition, the manufacturing cost is increased because the elastic member 204 needs to be manufactured independently of the other members such as the ultrasonic element 100.

SUMMARY OF THE INVENTION

In view of the above, the present invention provides an ultrasonic sensor capable of increasing the manufacturing efficiency and reducing the manufacturing cost.

In accordance with a first embodiment of the invention, there is provided an ultrasonic sensor, including: an ultrasonic element including an ultrasonic oscillator for sending, receiving or transceiving ultrasonic waves, an element body having an opening for passage of ultrasonic waves formed on one surface, the ultrasonic oscillator being arranged within the element body, and terminal portions protruding from the element body to feed an electric current to the ultrasonic oscillator; a housing having an opening formed on one surface for communication with the opening of the element body, the housing including a receiving portion for receiving the ultrasonic element and a positioning portion integrally formed with the receiving portion to position the ultrasonic element in place; and a printed wiring board arranged to interpose the ultrasonic element between the printed wiring board and the receiving portion of the housing, the terminal portions of the ultrasonic element being mounted to the printed wiring board.

The receiving portion may include a peripheral wall surrounding the ultrasonic element, the positioning portion being a plurality of ribs integrally formed with the peripheral wall to make contact with the ultrasonic element under pressure.

The receiving portion may include a peripheral wall surrounding the ultrasonic element, the positioning portion being a plurality of thin wall sections formed in the peripheral wall, the thickness of the thin wall sections in a radial direction of the peripheral wall being set smaller than the thickness of the remaining sections of the peripheral wall.

With the present invention, the ultrasonic element can positioned within the receiving portion using the positioning portion integrally formed with the housing. This eliminates the need to attach an elastic member to the ultrasonic element as in the conventional ultrasonic sensor, which makes it possible to increase the manufacturing efficiency. In addition, the manufacturing cost can be reduced because no need exists to independently manufacture an elastic member as in the conventional ultrasonic sensor.

BRIEF DESCRIPTION OF THE DRAWINGS

The objects and features of the present invention will become apparent from the following description of embodiments, given in conjunction with the accompanying drawings, in which.

DETAILED DESCRIPTION OF THE PREFERRED EMBODIMENTS

First Embodiment

Figure 1A:
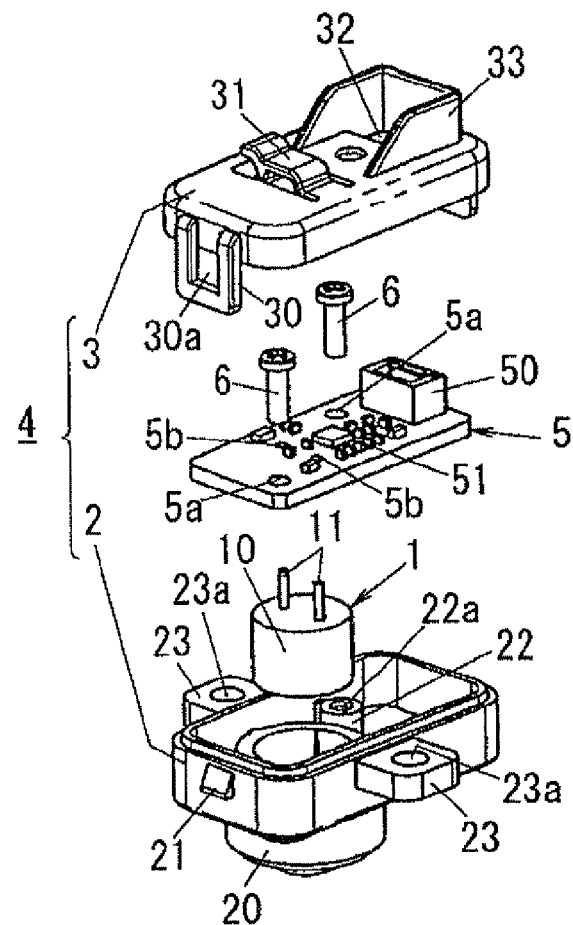
FIG. 1A is an exploded perspective view showing an ultrasonic sensor in accordance with a first embodiment of the present invention, FIG. 1B being a plan view showing a body thereof, FIG. 1C being an enlarged view of major portions shown in FIG. 1B, and FIG. 1D being a section view taken along line 1D-1D' in FIG. 1B.

An ultrasonic sensor in accordance with a first embodiment of the present invention will now be described with reference to the accompanying drawings which form a part hereof. In the following description, the direction running toward the upper and lower sides in FIG. 1A is defined as an up-down direction. Referring to FIGS. 1A through 1D, the ultrasonic sensor of the present embodiment includes an ultrasonic element 1, a housing 4 provided with a receiving portion 20 for storing the ultrasonic element 1 and a printed wiring board 5 arranged to interpose the ultrasonic element 1 between itself and the receiving portion 20. The ultrasonic element 1 includes terminal portions 11 mounted to the printed wiring board 5.

The ultrasonic element 1 is a so-called open ultrasonic element. The ultrasonic element 1 includes an ultrasonic oscillator (not shown) for sending, receiving or transceiving ultrasonic waves and a cylindrical element body 10 having a bottom with an opening for passage of ultrasonic waves. A pair of circular rod-shaped terminal portions 11 for feeding an electric current to the ultrasonic oscillator is provided on the upper portion of the element body 10 in such a fashion as to protrude upwards.

As shown in FIG. 1A, the housing 4 includes a rectangular box-shaped body 2 having an open top and a rectangular box-shaped cover 3 having an open bottom. The body 2 and the cover 3 are coupled together the openings thereof facing each other. A cylindrical receiving portion 20 is integrally formed in the lower portion of the body 2. On the longitudinal opposite end surfaces of the body 2, locking claws 21 are formed to protrude outwards. Rectangular frame portions 30 are provided on the longitudinal opposite end surfaces of the cover 3 to protrude downwards. Each of the frame portions 30 defines a locking hole 30a with which the corresponding locking claw can engage. The body 2 and the cover 3 are coupled together by bringing the locking claws 21 of the body 2 into engagement with the respective locking holes 30a of the cover 3.

Figure 1B:
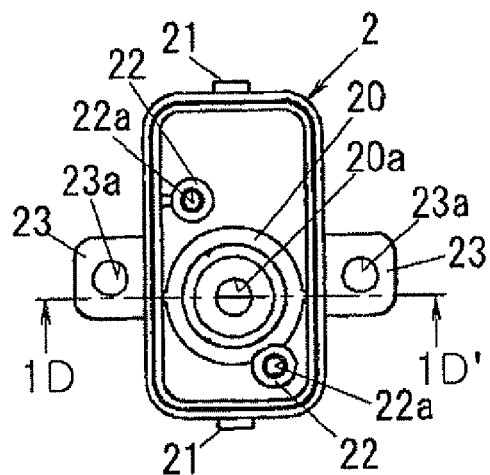

On the transverse opposite surfaces of the body 2, rectangular flat attachment pieces 23 are provided in such a fashion as to protrude outwards as illustrated in FIG. 1B. Each of the attachment pieces 23 has a circular attachment hole 23a in the central area thereof. Accordingly, the ultrasonic sensor of the present embodiment can be fixed to an external device by tightening screws through the attachment holes 23a. A pair of cylindrical boss portions 22 is formed within the body 2 to protrude upwards with the receiving portion 20 interposed therebetween. Female threads 22a are formed on the inner circumferential surfaces of the boss portions 22.

Figure 1C:
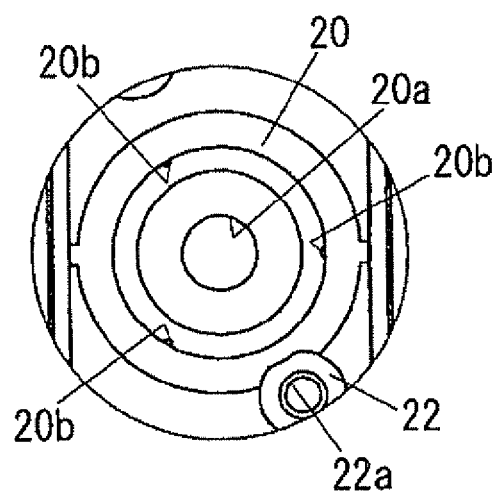
Figure 1D:
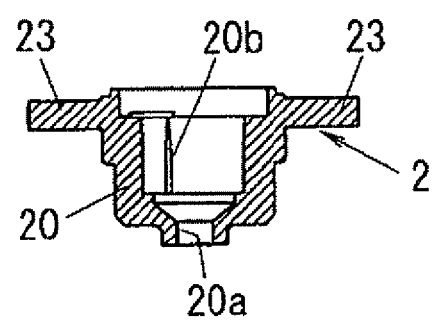

On the bottom of the receiving portion 20, an opening is formed as can be seen in FIG. 1D. The opening serves as a horn portion 20a that expands the wave-transceiving range of ultrasonic waves and decides the directivity of ultrasonic waves. On the inner surface of the peripheral wall of the receiving portion 20 surrounding the ultrasonic element 1, a plurality of (three, in the drawings) rod-shaped ribs 20b is integrally formed at even intervals in the circumferential direction as shown in FIG. 1C. Each of the ribs 20b has an upper end portion chamfered into a triangular cross-sectional shape as shown in FIG. 1D. Therefore, the ribs 20b play a role of so-called crush ribs that are crushed as the ultrasonic element 1 is pressed against the upper end portions of the ribs 20b. The ribs 20b serve as positioning portions for positioning the ultrasonic element 1 in place.

Figure 2A:
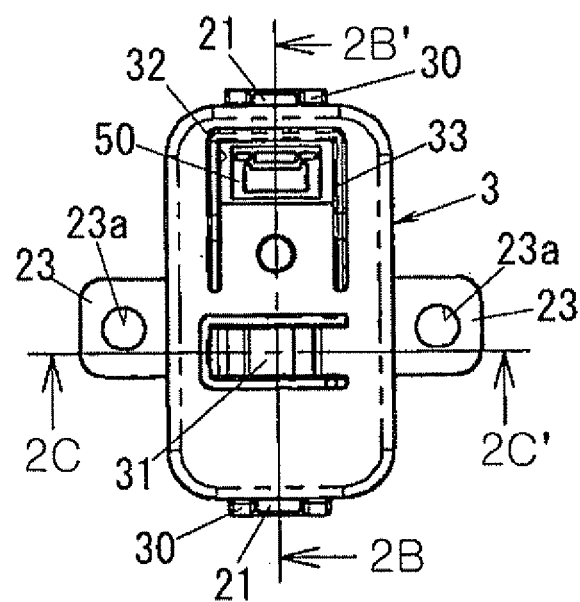
FIG. 2A is a plan view showing the ultrasonic sensor in an assembled state, FIG. 2B being a section view taken along line 2B-2B' in FIG. 2A, and FIG. 2C being a section view taken along line 2C-2C' in FIG. 2A.

Referring to FIGS. 1A and 2A, a tension sustaining portion 31 for sustaining the tension of a cable (not shown) drawn and wound from an external device is integrally formed with the central area of the upper surface of the cover 3. In one longitudinal end area of the upper surface of the cover 3, there is provided a rectangular window hole 32 into which a connector 50 is inserted as will be set forth later. A wall portion 33 having a substantially U-like cross-sectional shape is integrally formed along the peripheral edge of the window hole 32 in such a fashion as to protrude upwards. By surrounding the window hole 32 with the wall portion 33 in this manner, for example, it is possible to prevent an external force from exerting on the juncture of the cable and the connector 50.

Referring back to FIG. 1A, electronic parts 51 are mounted to the printed wiring board 5 to provide at least one of a drive circuit for driving the ultrasonic element 1 and a converter circuit for converting ultrasonic waves received by the ultrasonic element 1 to a wave-receiving signal. The drive circuit and the converter circuit are selectively adopted depending on the use of the ultrasonic sensor of the present embodiment. For example, the drive circuit may be employed if the ultrasonic sensor of the present embodiment is used to send ultrasonic waves. The converter circuit may be employed if the ultrasonic sensor of the present embodiment is used to receive ultrasonic waves (reflective waves). Needless to say, it may be possible to employ both the drive circuit and the converter circuit. A connector 50, to which one end portion of the cable is connected, is provided in one longitudinal end portion of the printed wiring board 5. Circular screw insertion holes 5a, into which set screws 6 are inserted, are provided in the portions of the printed wiring board 5 corresponding to the boss portions 22 of the body 2. The printed wiring board 5 is provided with a pair of circular terminal insertion holes 5b into which the terminal portions 11 of the ultrasonic element 1 are inserted. The terminal portions 11 are bonded to the circuit pattern of the printed wiring board 5 by performing a soldering work in a state that the terminal portions 11 are inserted into the terminal insertion holes 5b.

Figure 2B:
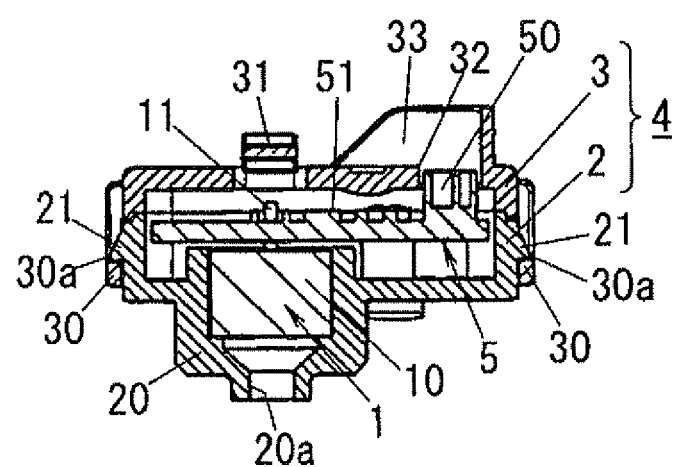
Figure 2C:
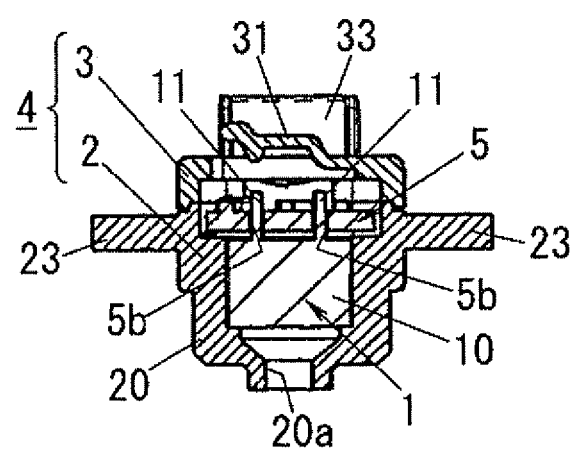

Next, description will be made on a method of assembling the ultrasonic sensor of the present embodiment. The ultrasonic element 1 is first stored in the receiving portion 20 with the terminal portions 11 facing upwards. Then, the printed wiring board 5 is placed on the upper surface of the ultrasonic element 1 while inserting the terminal portions 11 into the terminal insertion holes 5b. The set screws 6 are inserted through the screw insertion holes 5a and threadedly fixed to the female thread portions 22a of the boss portions 22, thereby securely attaching the printed wiring board 5 to the body 2. The terminal portions 11 are bonded to the circuit pattern of the printed wiring board 5 by soldering. Thereafter, the cover 3 and the body 2 are coupled together by bringing the locking claws 21 of the body 2 into engagement with the locking hole 30a of the cover 3. Thus, the ultrasonic sensor of the present embodiment is completely fabricated (see FIGS. 2A through 2C).

Figure 3A:
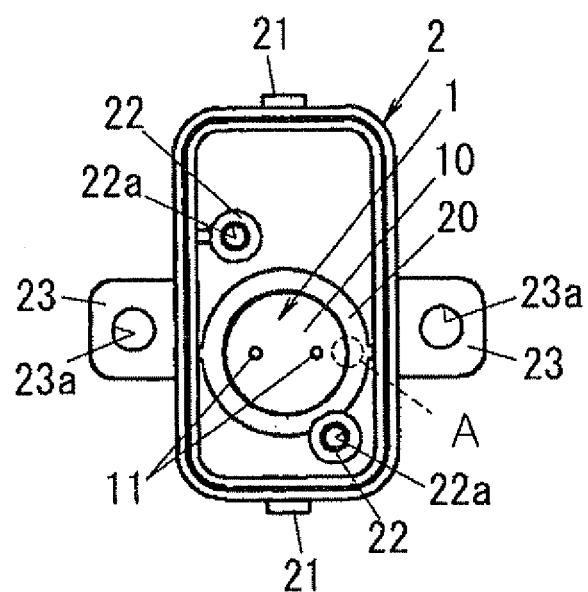
FIG. 3A is a plan view showing an ultrasonic element arranged in the body of the ultrasonic sensor and FIG. 3B is an enlarged view of the dot line area designated by "A" in FIG. 3A.
Figure 3B:
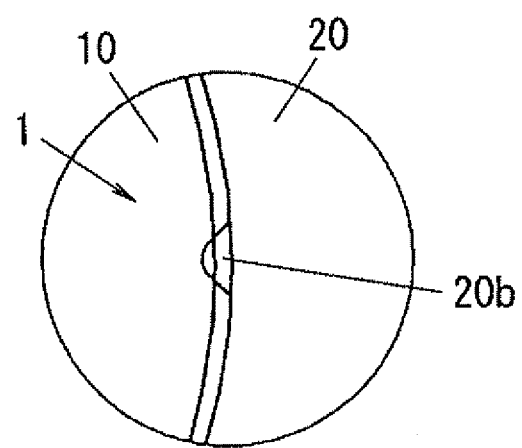

When storing the ultrasonic element 1 in the receiving portion 20, the ultrasonic element 1 is forcedly inserted into the receiving portion 20 to crush the upper end portions of the ribs 20b as shown in FIGS. 3A and 3B, whereby the ultrasonic element 1 makes contact with the ribs 20b under pressure. As a result, the ultrasonic element 1 is supported at three points by the ribs 20b with no looseness even though a gap exists between the ultrasonic element 1 and the receiving portion 20. Accordingly, the ultrasonic element 1 is positioned within the receiving portion 20 with no likelihood of variation in the positional relationship between the center of the horn portion 20a of the receiving portion 20 and the center of the opening of the ultrasonic element 1.

In the present embodiment described above, the ultrasonic element 1 can be positioned within the receiving portion 20 using the ribs 20b integrally formed with the housing 4. This eliminates the need to attach an elastic member to the ultrasonic element 1 as in the conventional ultrasonic sensor, which makes it possible to increase the manufacturing efficiency. In addition, the manufacturing cost can be reduced because no need exists to independently manufacture an elastic member as in the conventional ultrasonic sensor.

Second Embodiment

An ultrasonic sensor in accordance with a second embodiment of the present invention will now be described with reference to the accompanying drawings. The basic configuration of the present embodiment is the same as that of the first embodiment. Therefore, the same components will be designated by like reference symbols and redundant description thereof will be omitted. Just like the ultrasonic sensor of the first embodiment, the ultrasonic sensor of the present embodiment includes an ultrasonic element 1, a housing 4 provided with a receiving portion 20 for storing the ultrasonic element 1 and a printed wiring board 5 arranged to interpose the ultrasonic element 1 between itself and the receiving portion 20 (see FIGS. 4A to 5C). The ultrasonic element 1 includes terminal portions 11 mounted to the printed wiring board 5. In the present embodiment, as shown in FIGS. 4A to 4D, the peripheral wall of the receiving portion 20 surrounding the ultrasonic element 1 includes a plurality of (three, in the drawings) thin wall sections 20c in place of the ribs 20b of the first embodiment. The radial thickness of the thin wall sections 20c is set smaller than the radial thickness of the remaining sections. The thin wall sections 20c serve as positioning portions for positioning the ultrasonic element 1 in place.

Figure 4A:
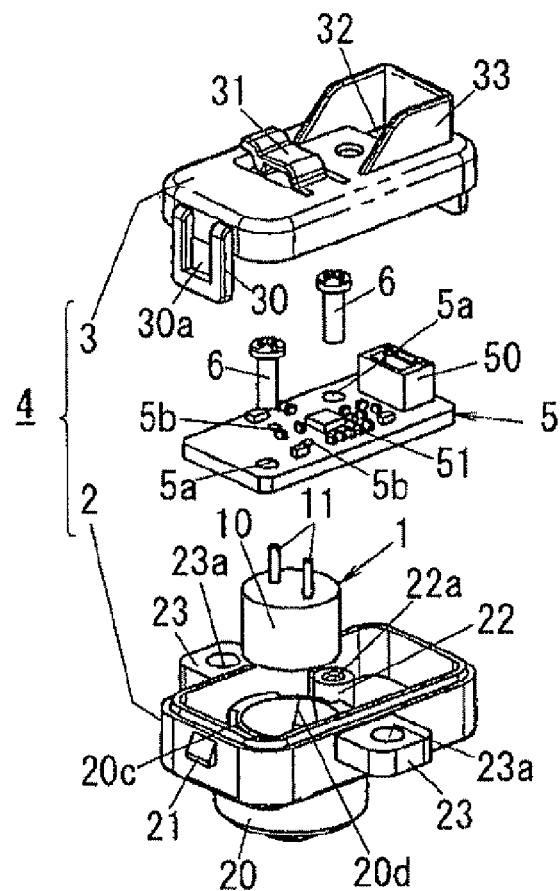
FIG. 4A is an exploded perspective view showing an ultrasonic sensor in accordance with a second embodiment of the present invention, FIG. 4B being a plan view showing a body thereof, FIG. 4C being an enlarged view of major portions shown in FIG. 4B, and FIG. 4D being a section view taken along line 4D-4D' in FIG. 4B.
Figure 4B:
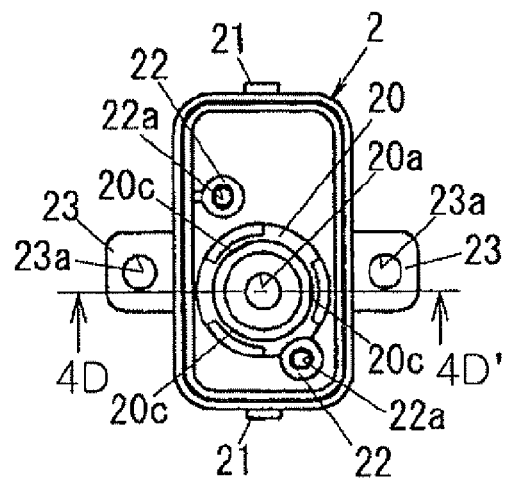
Figure 4C:
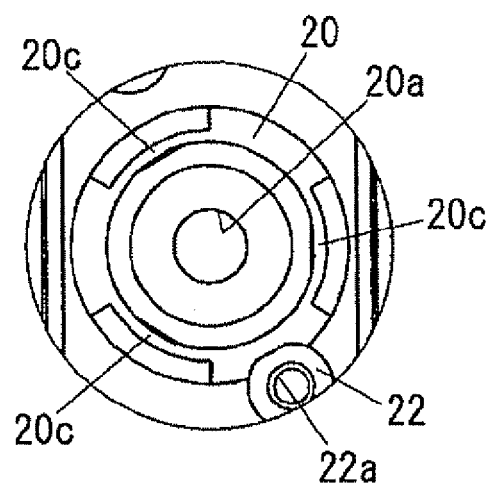
Figure 4D:
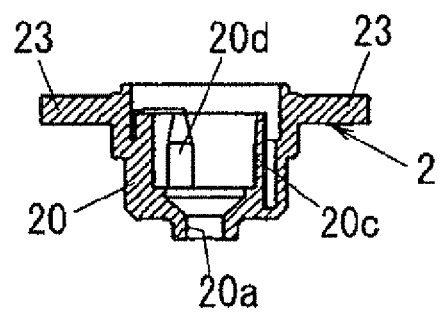
Figure 5A:
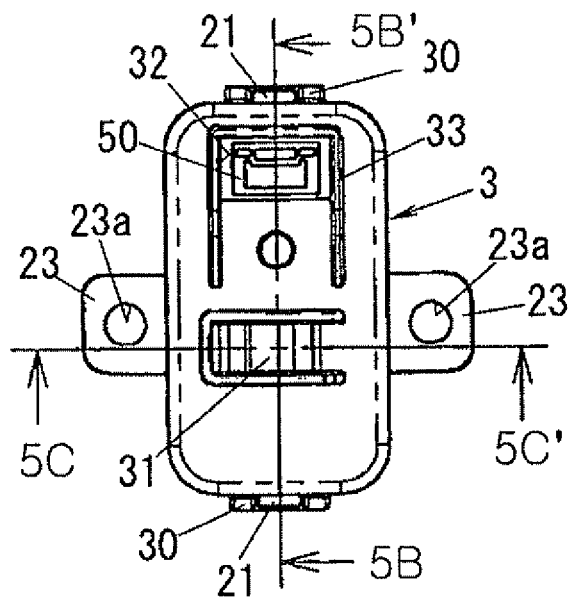
FIG. 5A is a plan view showing the ultrasonic sensor in an assembled state, FIG. 5B being a section view taken along line 5B-5B' in FIG. 5A, and FIG. 5C being a section view taken along line 5C-5C' in FIG. 5A.
Figure 5B:
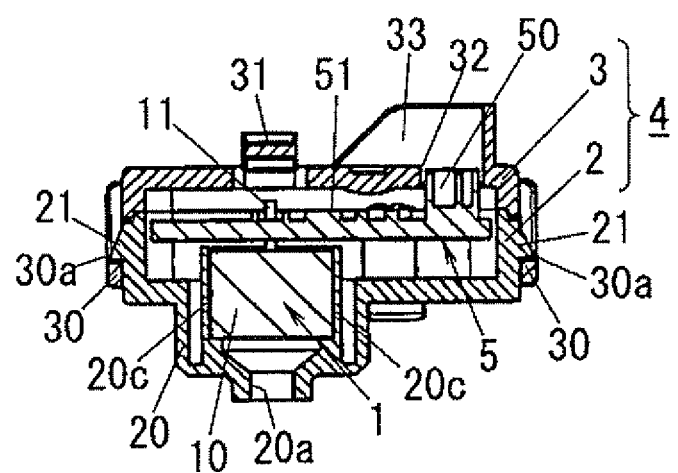
Figure 5C:
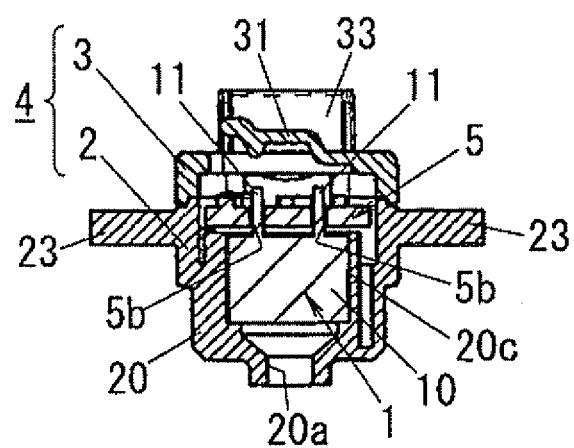
Figure 6A:
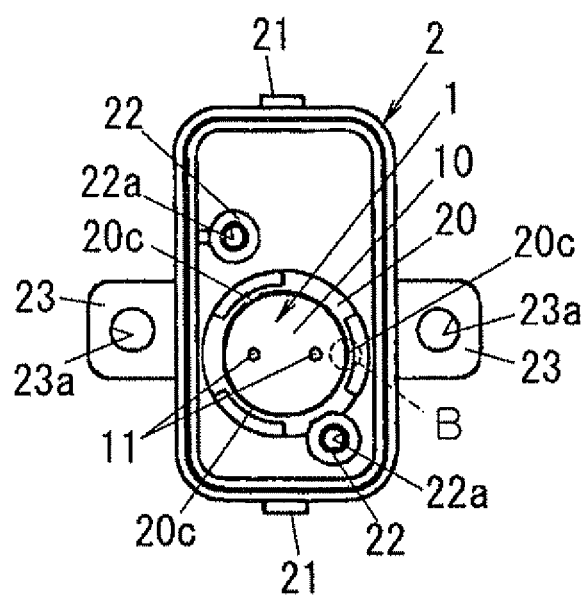
FIG. 6A is a plan view showing an ultrasonic element arranged in the body of the ultrasonic sensor and FIG. 6B is an enlarged view of the dot line area designated by "B" in FIG. 6A.
Figure 6B:
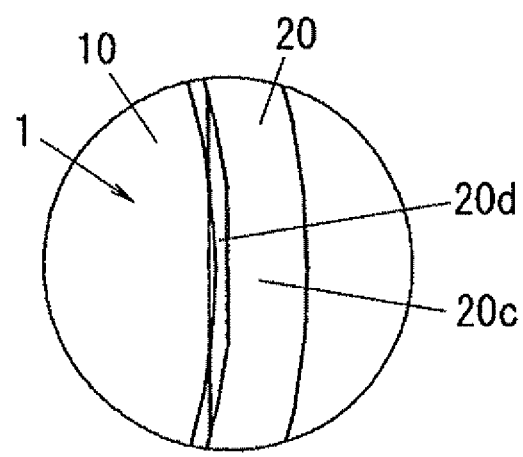
Figure 7A:
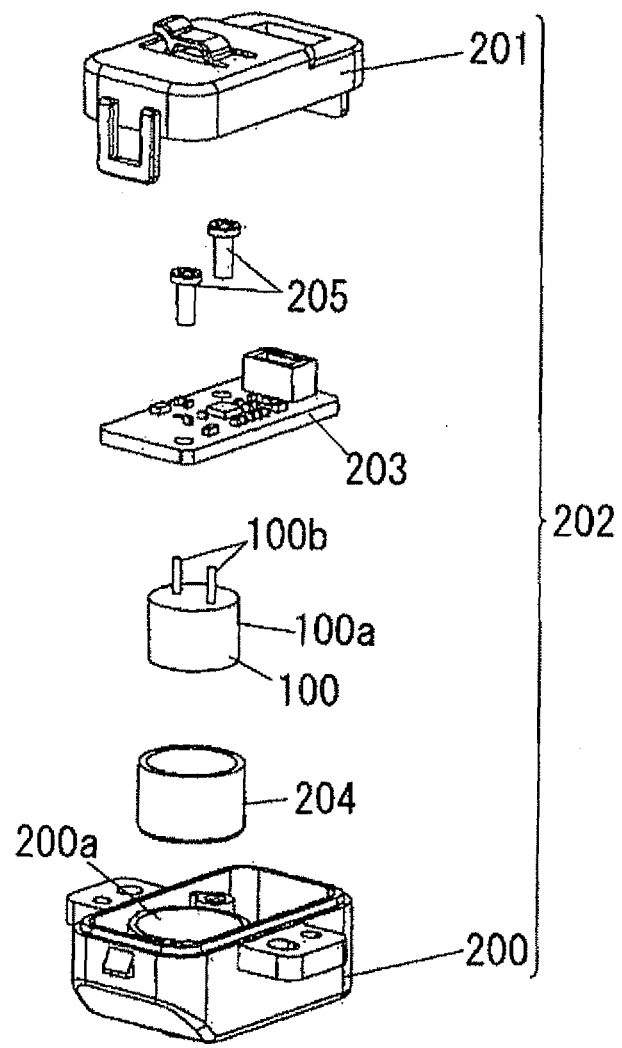
FIG. 7A is an exploded perspective view showing a conventional ultrasonic sensor and FIG. 7B is a section view thereof.
Figure 7B:
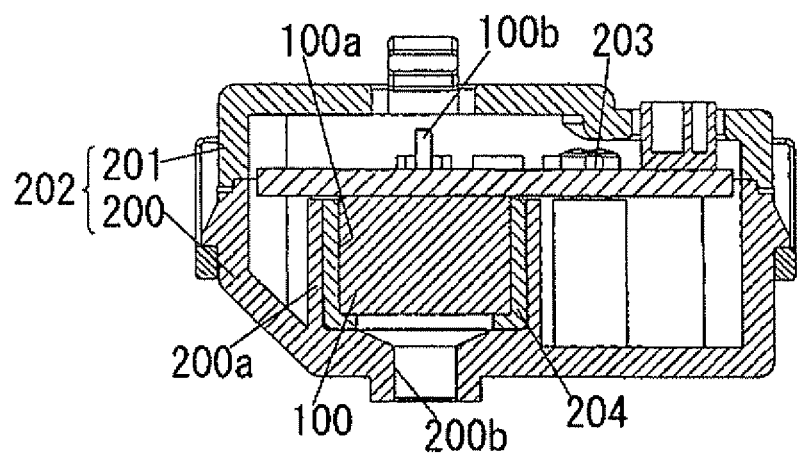

As shown in FIGS. 4B and 4C, the thin wall sections 20c are arranged at even intervals along the circumferential direction of the peripheral wall of the receiving portion 20. Since the thin wall sections 20c are smaller in thickness than other sections of the peripheral wall, they can be flexed in the radial direction. The storage portion 20 of the present embodiment is formed to have a diameter less than the diameter of the receiving portion 20 of the first embodiment but substantially equal to the diameter of the ultrasonic element 1.

In case of a conventional ultrasonic sensor, the ultrasonic element 1 cannot be received in the receiving portion 20 if the diameter of the receiving portion 20 is nearly equal to the diameter of the ultrasonic element 1 with no gap existing between the receiving portion 20 and the ultrasonic element 1. In the present embodiment, however, the thin wall sections 20c are formed in the peripheral wall of the receiving portion 20 as described above. Therefore, if the ultrasonic element 1 is forcedly inserted into the receiving portion 20, the thin wall sections 20c are pressed by the ultrasonic element 1 and flexed radially outwards. This creates a gap between the ultrasonic element 1 and the receiving portion 20, thereby making it possible to insert the ultrasonic element 1 in the receiving portion 20. Since the thin wall sections 20c tend to return radially inwards after inserting the ultrasonic element 1 in the receiving portion 20, the ultrasonic element 1 is supported at three points by the thin wall sections 20c with no looseness. Accordingly, the ultrasonic element 1 is positioned within the receiving portion 20 with no likelihood of variation in the positional relationship between the center of the horn portion 20a of the receiving portion 20 and the center of the opening of the ultrasonic element 1.

In the present embodiment described above, the ultrasonic element 1 can be positioned within the receiving portion 20 using the thin wall sections 20c integrally formed with the housing 4. This eliminates the need to attach an elastic member to the ultrasonic element 1 as in the conventional ultrasonic sensor, which makes it possible to increase the manufacturing efficiency. In addition, the manufacturing cost can be reduced because no need exists to independently manufacture an elastic member as in the conventional ultrasonic sensor.

In the present embodiment, as shown in FIGS. 4A, 4D, 6A and 6B, crush ribs 20d having top end portions chamfered into a trapezoidal cross-sectional shape are integrally formed with the inner surfaces of the thin wall sections 20c. The ultrasonic element 1 is forcedly inserted into the receiving portion 20 to crush the upper end portions of the crush ribs 20d, whereby the ultrasonic element 1 makes contact with the crush ribs 20d under pressure. This makes it possible to reliably position the ultrasonic element 1 within the receiving portion 20.

While the invention has been shown and described with respect to the embodiments, it will be understood by those skilled in the art that various changes and modification may be made without departing from the scope of the invention as defined in the following claims.

What is claimed is:
1. An ultrasonic sensor, comprising:
   an ultrasonic element including an ultrasonic oscillator for sending, receiving or transceiving ultrasonic waves, an element body having an opening for passage of ultrasonic waves formed on one surface, the ultrasonic oscillator being arranged within the element body, and terminal portions protruding from the element body to feed an electric current to the ultrasonic oscillator;

a housing having an opening formed on one surface for communication with the opening of the element body, the housing including a receiving portion for receiving the ultrasonic element and a positioning portion integrally formed with the receiving portion to position the ultrasonic element in place; and a printed wiring board arranged to interpose the ultrasonic element between the printed wiring board and the receiving portion of the housing, the terminal portions of the ultrasonic element being mounted to the printed wiring board.

2. The ultrasonic sensor of claim 1, wherein the receiving portion includes a peripheral wall surrounding the ultrasonic element, the positioning portion being a plurality of ribs integrally formed with the peripheral wall to make contact with the ultrasonic element under pressure.

3. The ultrasonic sensor of claim 1, wherein the receiving portion includes a peripheral wall surrounding the ultrasonic element, the positioning portion being a plurality of thin wall sections formed in the peripheral wall, the thickness of the thin wall sections in a radial direction of the peripheral wall being set smaller than the thickness of the remaining sections of the peripheral wall.

4. The ultrasonic sensor of claim 1, wherein the positioning portion of the housing is formed by deformable elements which are adapted to contact the ultrasonic element under pressure after said ultrasonic element has been forcedly inserted into the receiving portion.

\* \* \* \* \*